(12) United States Patent
Ichikawa

(10) Patent No.: US 10,653,568 B2
(45) Date of Patent: May 19, 2020

(54) DISPOSABLE PULL-ON DIAPER

(71) Applicant: UNICHARM CORPORATION, Ehime (JP)

(72) Inventor: Makoto Ichikawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 1138 days.

(21) Appl. No.: 14/896,542

(22) PCT Filed: May 19, 2014

(86) PCT No.: PCT/JP2014/063251
§ 371 (c)(1),
(2) Date: Dec. 7, 2015

(87) PCT Pub. No.: WO2014/199784
PCT Pub. Date: Dec. 18, 2014

(65) Prior Publication Data
US 2016/0128875 A1     May 12, 2016

(30) Foreign Application Priority Data

Jun. 14, 2013 (JP) ................................. 2013-126116

(51) Int. Cl.
*A61F 13/15* (2006.01)
*A61F 13/20* (2006.01)
(Continued)

(52) U.S. Cl.
CPC ...... *A61F 13/49015* (2013.01); *A61F 13/496* (2013.01); *A61F 13/4915* (2013.01);
(Continued)

(58) Field of Classification Search
CPC ............ A61F 13/49015; A61F 13/4915; A61F 13/4942; A61F 13/496; A61F 13/53; A61F 2013/49093; A61F 2013/530868
See application file for complete search history.

(56) References Cited

U.S. PATENT DOCUMENTS

2003/0088230 A1* 5/2003 Balogh ............. A61F 13/49413
604/385.101
2006/0264859 A1* 11/2006 Tsuji ................. A61F 13/49012
604/385.28
(Continued)

FOREIGN PATENT DOCUMENTS

EP         2 561 847 A1      2/2013
JP         2002-320641 A    11/2002
(Continued)

OTHER PUBLICATIONS

European supplementary Search Report from corresponding European application No. 14810466.4 dated Jun. 3, 2016 (10 pgs).
(Continued)

*Primary Examiner* — Michele M Kidwell
(74) *Attorney, Agent, or Firm* — Osha Liang LLP

(57) ABSTRACT

A disposable pull-on diaper that keeps in close contact with a wearer's crotch region includes a lower torso cover and an absorbent chassis. The absorbent chassis has a front end portion overlapping a front waist region of the lower torso cover and a front end portion of the front end portion is joined to an elastic region in the lower torso cover. A front end adjoining portion of the front end portion is not joined to the elastic region. An area in the absorbent chassis being adjacent the front end adjoining portion on the side of the crotch region is joined to an inelastic region defined on the side closer to the crotch region than to the elastic region. The absorbent body contained in the absorbent chassis extends at least from the crotch region to the front end adjoining portion. The front end portion in the front end portion of the absorbent chassis is defined by a portion of the cover sheet wrapping the absorbent body which extends outward beyond the absorbent body.

5 Claims, 10 Drawing Sheets

(51) Int. Cl.
- *A61F 13/49* (2006.01)
- *A61F 13/496* (2006.01)
- *A61F 13/53* (2006.01)
- *A61F 13/491* (2006.01)
- *A61F 13/494* (2006.01)

(52) U.S. Cl.
CPC .......... *A61F 13/4942* (2013.01); *A61F 13/53* (2013.01); *A61F 2013/49093* (2013.01); *A61F 2013/530868* (2013.01)

(56) References Cited

U.S. PATENT DOCUMENTS

| | | |
|---|---|---|
| 2013/0102987 A1 | 4/2013 | Mukai et al. |
| 2013/0338623 A1 | 12/2013 | Kinoshita et al. |
| 2015/0223994 A1 | 8/2015 | Ichikawa et al. |

FOREIGN PATENT DOCUMENTS

| | | |
|---|---|---|
| JP | 2005-103178 A | 4/2005 |
| JP | 3153770 U | 8/2009 |
| JP | 5186058 | 1/2013 |
| WO | WO 2012/117723 A1 | 9/2012 |
| WO | WO 2012/137598 A1 | 10/2012 |
| WO | WO 2014/024326 A1 | 2/2014 |

OTHER PUBLICATIONS

International Search Report from corresponding PCT application No. PCT JP2014/063251 dated Jul. 29, 2014 (4 pgs).

\* cited by examiner

DISPOSABLE PULL-ON DIAPER

RELATED APPLICATION

This application is a 35 U.S.C. § 371 national phase filing of International Patent Application No. PCT/JP2014/063251, filed May 19, 2014, through which and to which priority is claimed under 35 U.S.C. § 119 to Japanese Patent Application No. 2013-126116, filed Jun. 14, 2013, the complete disclosure of which are hereby expressly incorporated herein by reference.

TECHNICAL FIELD

The present disclosure relates to disposable pull-on diapers and more specifically to disposable pull-on diapers preferred for good fit of a crotch region of the diaper to the diaper wearer's body.

BACKGROUND

Conventionally, disposable pull-on diapers are known and the disposable pull-on diapers directed to assure good fit of the crotch region of the diaper to the wearer's body are also known.

For example, the pant-type absorbent articles exemplarily disclosed in JP 2002-320641 (Patent Literature 1) are women's absorbent undergarments and disposable diapers each composed of a pant-type chassis and an absorbent structure including an absorbent body fixed to an interior surface of the pant-type cover. The absorbent structure has joining regions to the chassis along end portions thereof opposite in the longitudinal direction and along intermediate portions defined between these opposite end portions. Between each pair of the adjacent joining regions, a non-joining region is formed in which the absorbent structure is not joined to the chassis. Waist elastic elements extending in a width direction thereof are attached under tension to the chassis.

CITATION LIST

Patent Literature

{PTL 1}: JP 2002-320641 A

SUMMARY

Technical Problem

When the elastic elements contract on the bottom surface side of the absorbent structure, this absorbent structure is deformed so as to be convexly toward the wearer of the absorbent article and to be put in close contact with the wearer's skin whether the elastic elements extend in the longitudinal direction of the absorbent structure or in the lateral direction of the chassis. However, for male incontinence patients, the absorbent structure deformed in such manner may compress the male genitalia and it may be hard to say "this absorbent article ensures comfortable fit".

An object of the present invention is to provide a disposable pull-on diaper improved so that, particularly when it is used as men's diapers, good fit of the diaper to the wearer's crotch region may be ensured.

Solution to Problem

An object of the present invention is to improve the disposable pull-on diaper having a lateral direction and a longitudinal direction and including a lower torso cover which assumes a tubular shape and defines at least a front waist region and a back waist region among the front waist region, the back waist region and a crotch region, an absorbent chassis provided with an absorbent structure and extending between the front waist region and the back waist region and having a front end portion and a back end portion adapted to overlap the front waist region and the back waist region, respectively, a waist opening and a pair of leg-openings.

The present invention further includes arrangements described below: The lower torso cover has an elastic region in which a plurality of elastic elements extend in a lateral direction of the lower torso cover and are contractibly secured under tension. The absorbent chassis is composed of an absorbent body included in the absorbent structure, a liquid-permeable body side liner and a liquid-impermeable backsheet and includes a cover sheet to cover the absorbent body wherein the cover sheet extends outward in the longitudinal direction beyond the absorbent body. The front end portion of the absorbent chassis has a front end portion joined to the lower torso cover in the elastic region and a front end adjoining portion not joined to the elastic region and extending adjacent to the front end portion on the side of the crotch region wherein an area extending adjacent to the front end adjoining portion on the side of the crotch region is joined to an inelastic region extending adjacent to the front end adjoining portion on the side of the crotch region and including none of the elastic elements extending in the lateral direction. The absorbent body extends at least from the crotch region to the front end adjoining portion and the front end portion is defined by the portion of the cover sheet extending outward beyond the absorbent body.

The term "pull-on diaper" used in the present specification refers to a diaper having a waist-opening and a pair of leg-openings adapted to put the diaper on the wearer's body by inserting the wearer's legs through respective leg-openings and then, pull up the diaper to the wearer's waist line. The term "disposable" used in the present specification ordinarily refers to the diaper intended to be discarded after a single use.

Advantageous Effects of Invention

In the disposable pull-on diapers according to one or more embodiments of the present invention, a portion of the front end portion of the absorbent chassis overlapping with the lower torso cover, i.e., the front end adjoining portion including the absorbent body is not joined to the elastic region in the lower torso cover. Consequently, the front end adjoining portion including the absorbent body roughly gets wrinkled when the elastic region elastically contracts in the lateral direction of the lower torso cover. In consequence, an apparent width of the absorbent chassis is reduced and the absorbent chassis is deformed so as to protrude outward from the diaper. Such deformation makes an appearance also in the other regions being adjacent from below to the front end adjoining portion and creates a space in the absorbent chassis appropriate to receive the male genitalia. The absorbent chassis being capable for reception of the male genitalia makes it easy to fit the diaper to the wearer's crotch region.

BRIEF DESCRIPTION OF DRAWINGS

The accompanying drawings illustrate specific embodiments of the present invention including optional and preferred embodiments as well as essential features of the invention.

DESCRIPTION OF EMBODIMENTS

The disposable pull-on diaper according to the present invention will be described in details hereunder with reference to the accompanying drawings. The embodiments described hereunder relate to the diapers illustrated in FIGS. 1 through 9 and including both optional and preferred features as well as those features which are essential features of the present invention.

Figure 1:
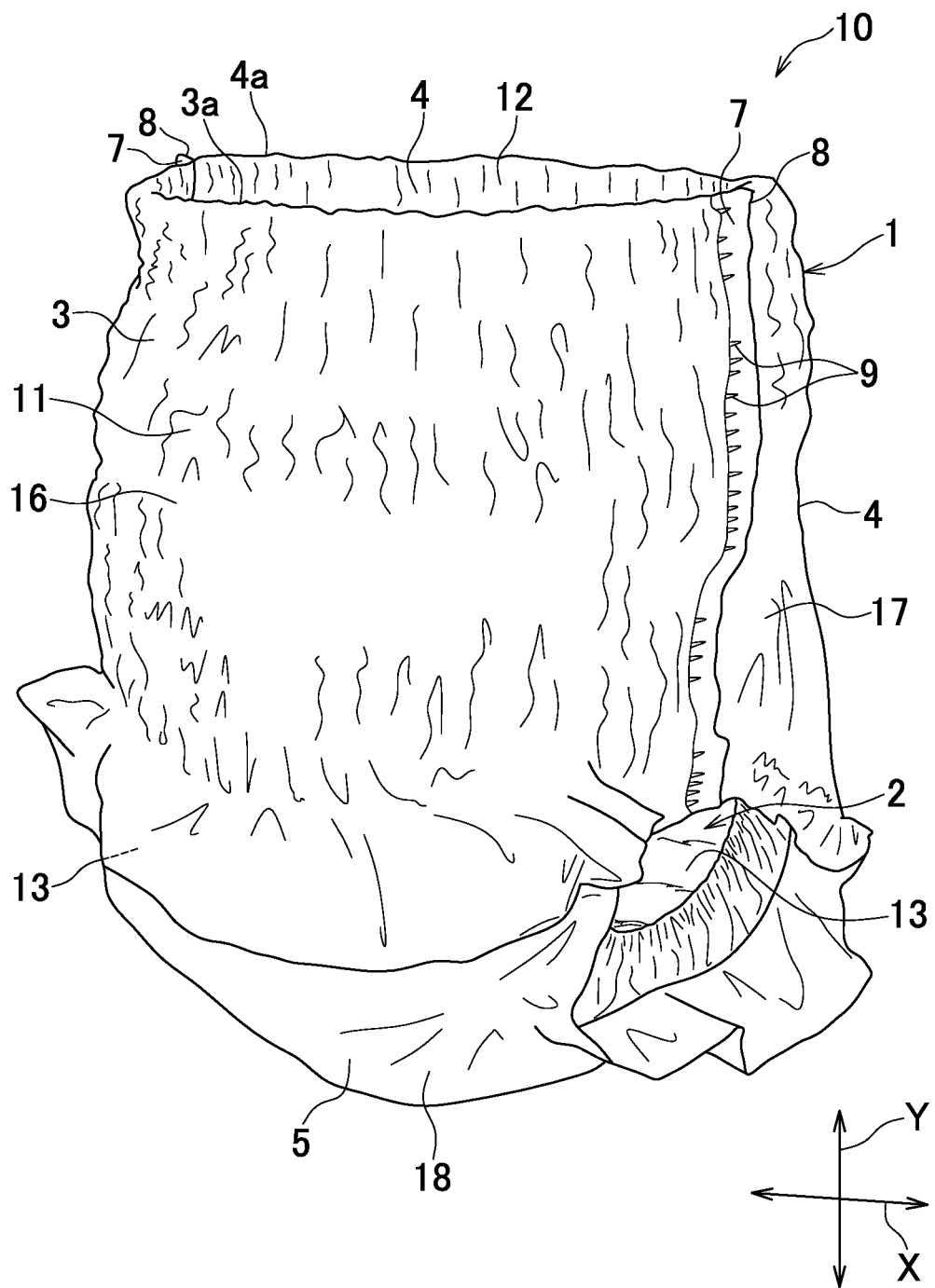
FIG. 1 is a perspective view of a disposable pull-on diaper.

FIG. 1 is a perspective view exemplarily illustrating an adult-sized disposable pull-on diaper 10 according to one of the embodiments of the present invention. The diaper 10 is effective to be used for a male person with incontinence and includes a lower torso cover 1 and an absorbent chassis 2 (see FIG. 2) attached to the lower torso cover 1. While it is required for the lower torso cover 1 to include at least a front waist region and a back waist region of the front waist region, the back waist region and a crotch region, the accompanying drawings exemplarily illustrate the lower torso cover 1 fully including the front waist region 3, the back waist region 4 and the crotch region 5. The front waist region 3 and the back waist region 4 are joined to each other at a series of seams 9 made along respective side edges 7, 8 thereof with use of for example, the ultrasonic process, so that a waist region 11 to assume a tubular shape when the diaper 10 on the wearer's body, a waist opening 12 and a pair of leg openings 13 are defined. The lower torso cover 1 includes a front exterior sheet 16 extending in the front waist region 3 and a portion of the crotch region 5, a back exterior sheet 17 extending in the back waist region 4 and a portion of the crotch region 5 and a central exterior sheet 18 extending in the crotch region 5. In FIG. 1, a lateral direction and a longitudinal direction of the diaper 10 are indicated by X and Y, respectively.

Figure 2:
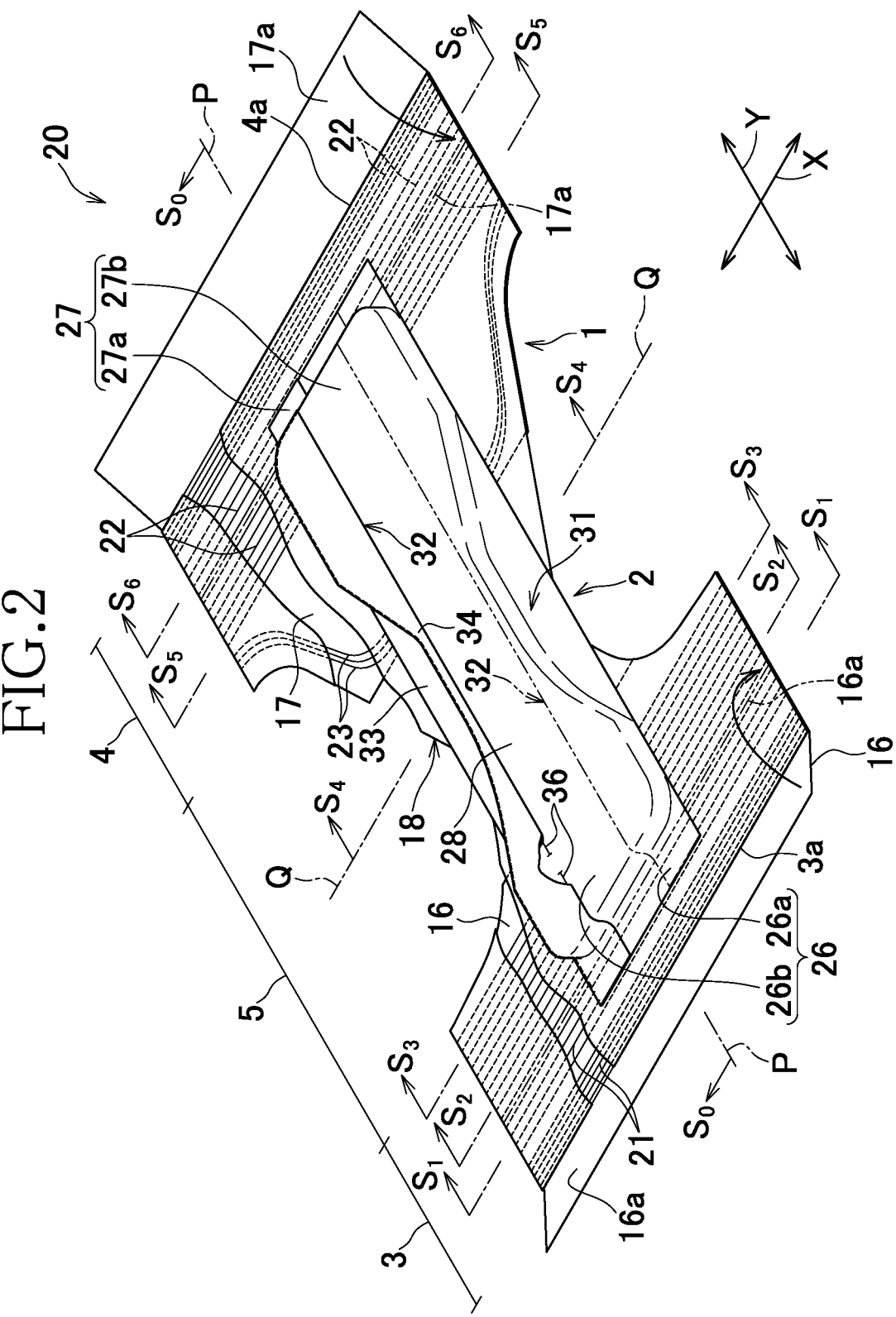
FIG. 2 is a partially cutaway perspective view of the diaper extended in a longitudinal direction and a lateral direction after seams formed along both lateral edges of the diaper have been ripped open.

FIG. 2 is a partially cutaway perspective view illustrating an interior side of the diaper 10 wherein the seams 9 at which the front waist region 3 and the back waist region 4 are joined to each other in the diaper 10 illustrated in FIG. 1 have been ripped open and the diaper 10 has been extended in the lateral direction X and in the longitudinal direction Y.

As will be apparent from FIG. 2, the lower torso cover 1 is generally sandglass-shaped and includes a central exterior sheet 18 extending over the front waist region 3, the back waist region 4 and the crotch region 5, a front exterior sheet 16 joined to the outside of the central exterior sheet 18 and a back exterior sheet 17 joined to the outside of the central exterior sheet 18 in the same manner as the front exterior sheet 16 (see FIG. 1). Between the front exterior sheet 16 and the central exterior sheet 18, a plurality of front waist elastic elements 21 are contractibly secured under tension in the lateral direction X. In the same manner, a plurality of back waist elastic elements 22 are contractibly interposed between the back exterior sheet 17 and the central exterior sheet 18. In a similar manner, a plurality of back waist elastic elements 22 are contractibly secured under tension in the lateral direction X. In addition, between the back exterior sheet 17 and the central exterior sheet 18, a plurality of leg elastic elements 23 extending in the lateral direction X so as to curve convexly toward the front waist region 3 are contractibly interposed at least partially under tension. In the lower torso cover 1, an area in which the front waist elastic elements 21 are present defines a front elastic region and an area in which the back waist elastic elements 22 are present defines a back elastic region. An area in which the back leg elastic elements 23 are present defines a back leg elastic region. Meanwhile, in a front portion of the crotch region 5 defined between a center line Q extending in the lateral direction and the front waist region 3 and a portion of the front waist region 3 adjacent to the crotch region 5, none of the elastic elements extend in the lateral direction X, namely, these portions define inelastic regions. In the diaper 10, the front exterior sheet 16 and the back exterior sheet 17 are partially folded back onto the top surface of the diaper 10 along an edge 3a of the front waist region 3 and an edge 4a of the back waist region 4, respectively. In this regard, FIG. 2 indicates fully folded back portions 16a, 17a along imaginary lines and these portions 16a, 17a before fully folded back along solid lines.

As will be apparent from FIG. 2, the absorbent chassis 2 has a front end portion 26 including a front end portion 26a and a front end adjoining portion 26b, and a back end portion 27 including a back end portion 27a and a back end adjoining portion 27b. More specifically, the absorbent chassis 2 has the front end portion 26 extending from the crotch region 5 of the lower torso cover 1 to the front waist region 3, overlapping the top surface of the front waist region 3 and joined to the front waist region 3, the back end portion 27 extending from the crotch region 5 to the back waist region 4, overlapping the top surface of the back waist region 4 and joined to the back waist region 4 and an intermediate region 28 joined to the crotch region 5. The absorbent chassis 2 includes an absorbent structure 31 having a rectangular shape in planar view and a pair of leakage-barrier cuffs 32 allocated on lateral sides of the absorbent structure 31 opposite to each other in the lateral direction X. In FIG. 2, one of the leakage-barrier cuffs 32 is indicated by a solid line and the other is indicated by a two-dot chain line (imaginary line). In this regard, as will be apparent from FIG. 2, the front end adjoining portion 26b is adjoining to the front end portion 26a on the side of the crotch region 5 and the back end adjoining portion 27b is adjoining to the back end portion 27a on the side of crotch region 5. According to the present embodiment, the lateral edges in the lateral direction X of the crotch region 5 define the leg-openings 13. The term "the front waist region 3 and the back waist region 4" used in the present embodiment refer to the regions located above the leg-openings 13 as seen in FIG. 1. The term "elastic regions" used for the present invention refer to the regions in which the elastic elements extending in parallel to each other at intervals of 15 mm or less and contractibly secured under tension.

Each of the leakage-barrier cuffs 32 has a proximal edge portion 33 fixed to the absorbent structure 31 and a distal edge portion 34 not joined to the absorbent structure 31 in the crotch region 5 so as to be spaced away therefrom wherein the distal edge portion 34 includes one or more elastic elements contractibly secured thereto under tension. The distal edge portion 34 is fixed to the front and back end adjoining portions 26b, 27b in the front and back end portions 26, 27 of the absorbent structure 31. With the diaper 10 being in the state illustrated in FIG. 1, the elastic elements 36 in these leakage-barrier cuffs 32 contract. In consequence, the respective distal edge portions 34 of the leakage-barrier cuffs 32 are spaced away from the absorbent structure 31 toward the wearer's body at least in the crotch region 5. Thus, the respective leakage-barrier cuffs 32 take postures upstanding postures on the absorbing surface of the absorbent structure 31.

Figure 3:
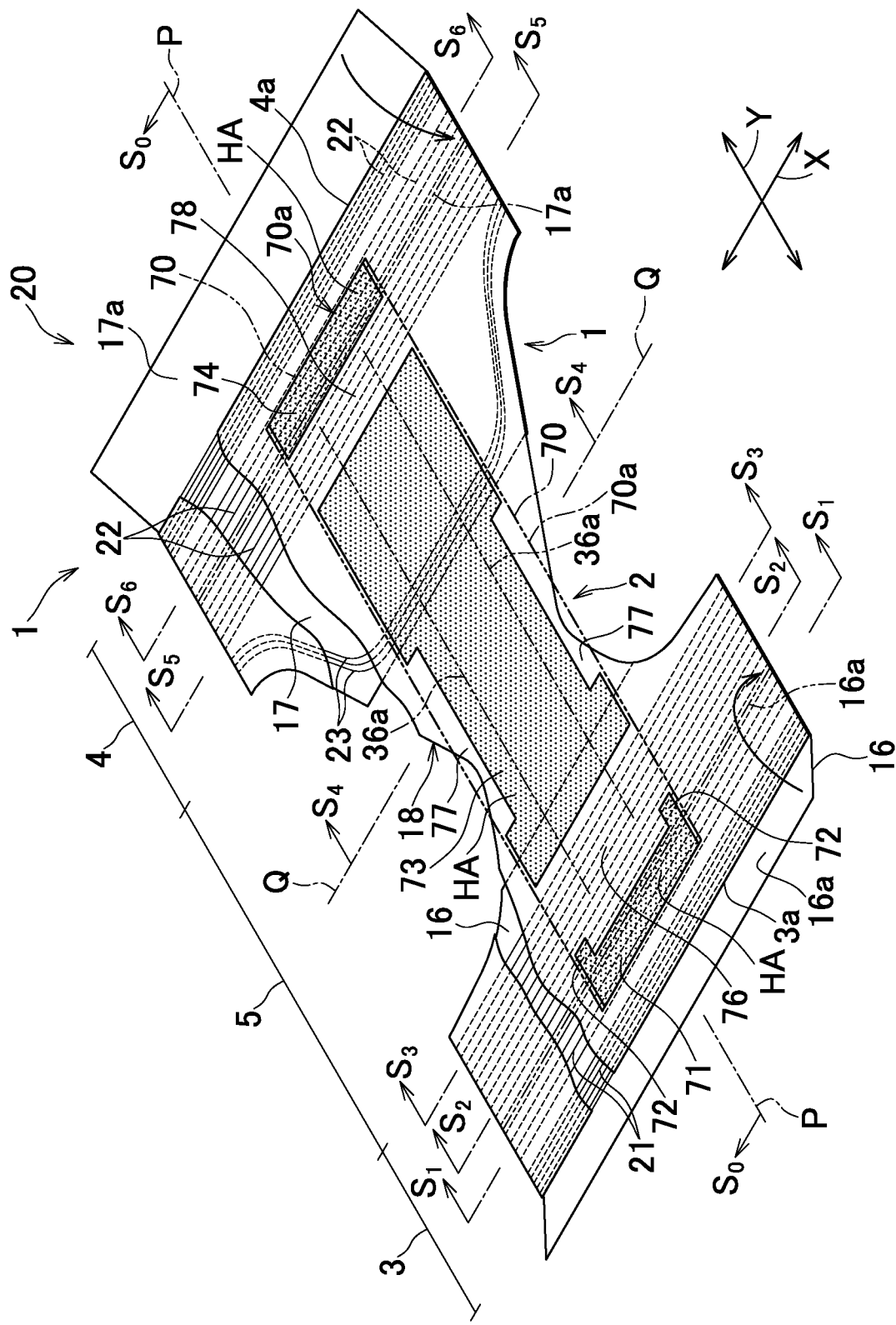
FIG. 3 is a perspective view of a lower torso cover illustrated in FIG. 2.

FIG. 3 is a perspective view of the lower torso cover 1 illustrated FIG. 2 wherein a position of the absorbent chassis 2 is indicated by a two-dot chain line (imaginary line) 70. Inboard of a rectangle 70a defined by the imaginary line 70, coated regions 71 through 74, for example, with hot melt adhesive HA for joining of the absorbent chassis 2 are indicated by a plurality of dots. Also inboard of the rectangle 70a, non-coated regions 76 through 78 are indicated, to which any amount of hot melt adhesive HA is distributed. Furthermore, also inboard of the rectangle 70a, portions 36a among the elastic elements 36, which are left to be contractible, are indicated by imaginary lines.

Figure 4:
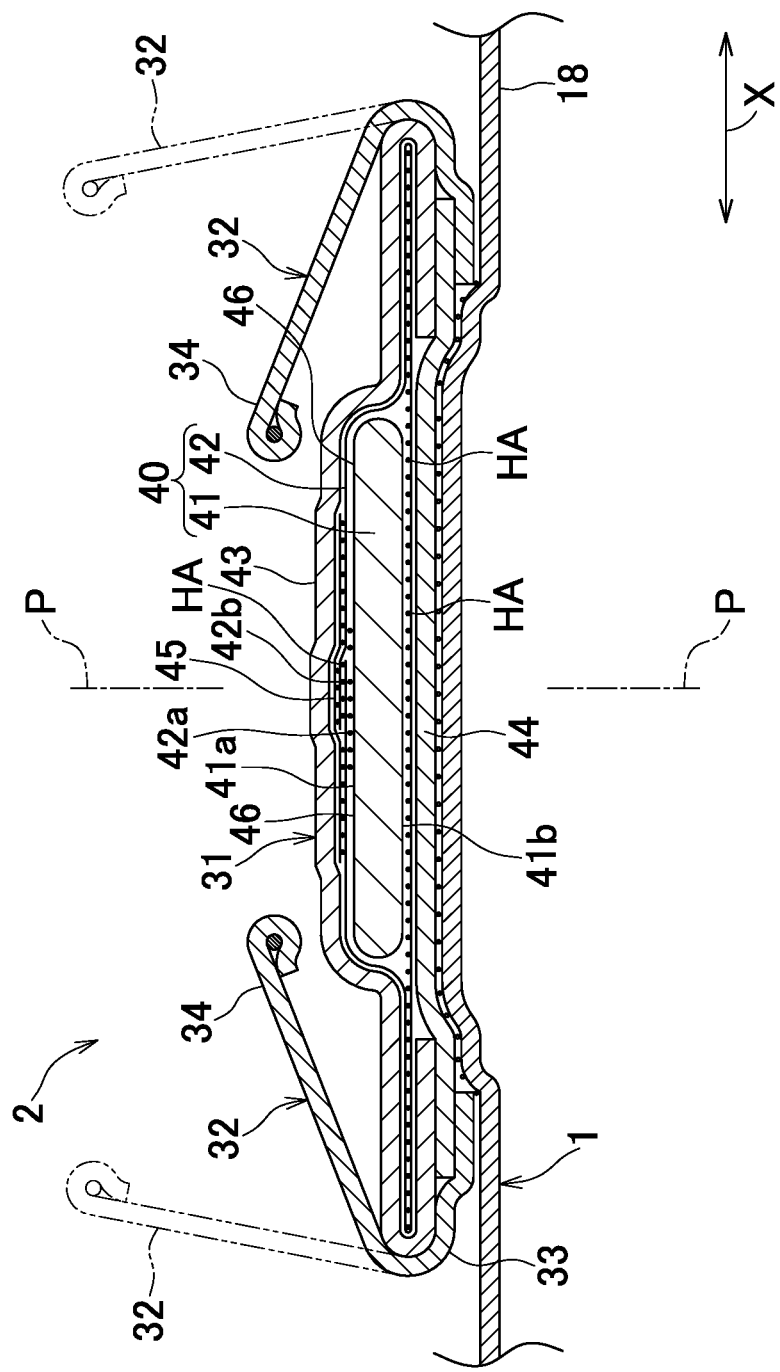
FIG. 4 is a sectional view taken along line S4 in FIG. 2.
Figure 5:
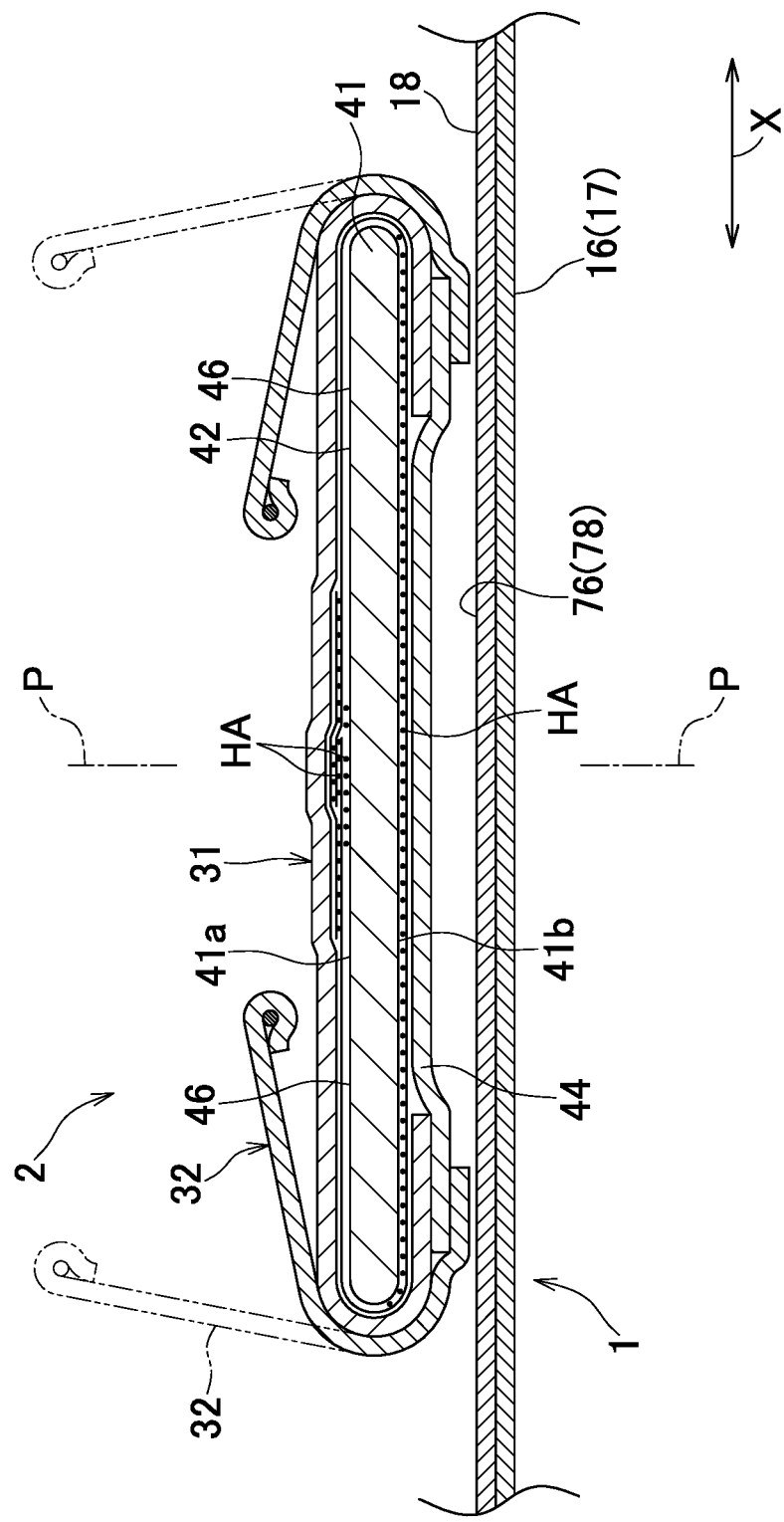
FIG. 5 is a sectional view taken along line S3 of S5 in FIG. 2.
Figure 6:
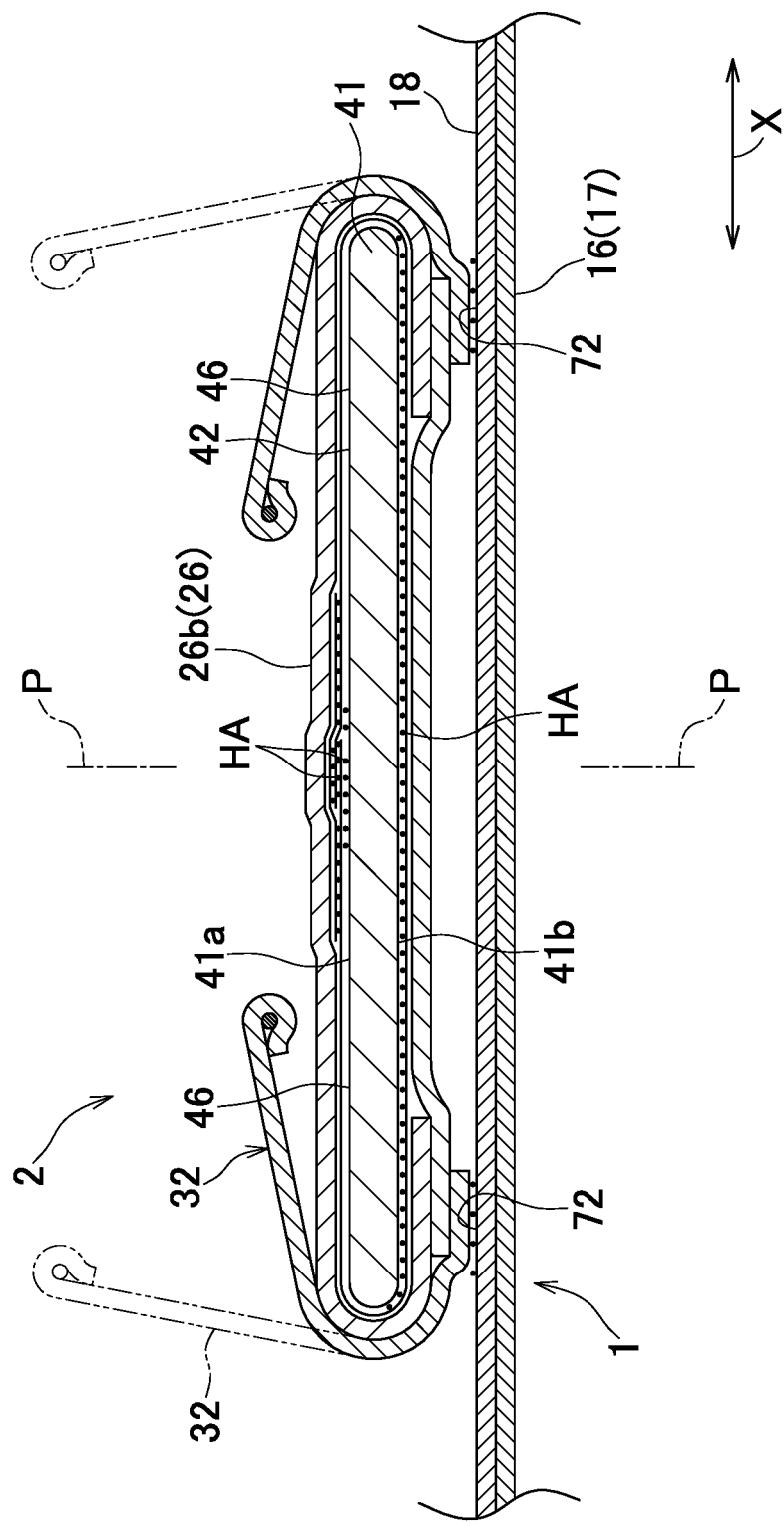
FIG. 6 is a sectional view taken along line S2 in FIG. 2.
Figure 7:
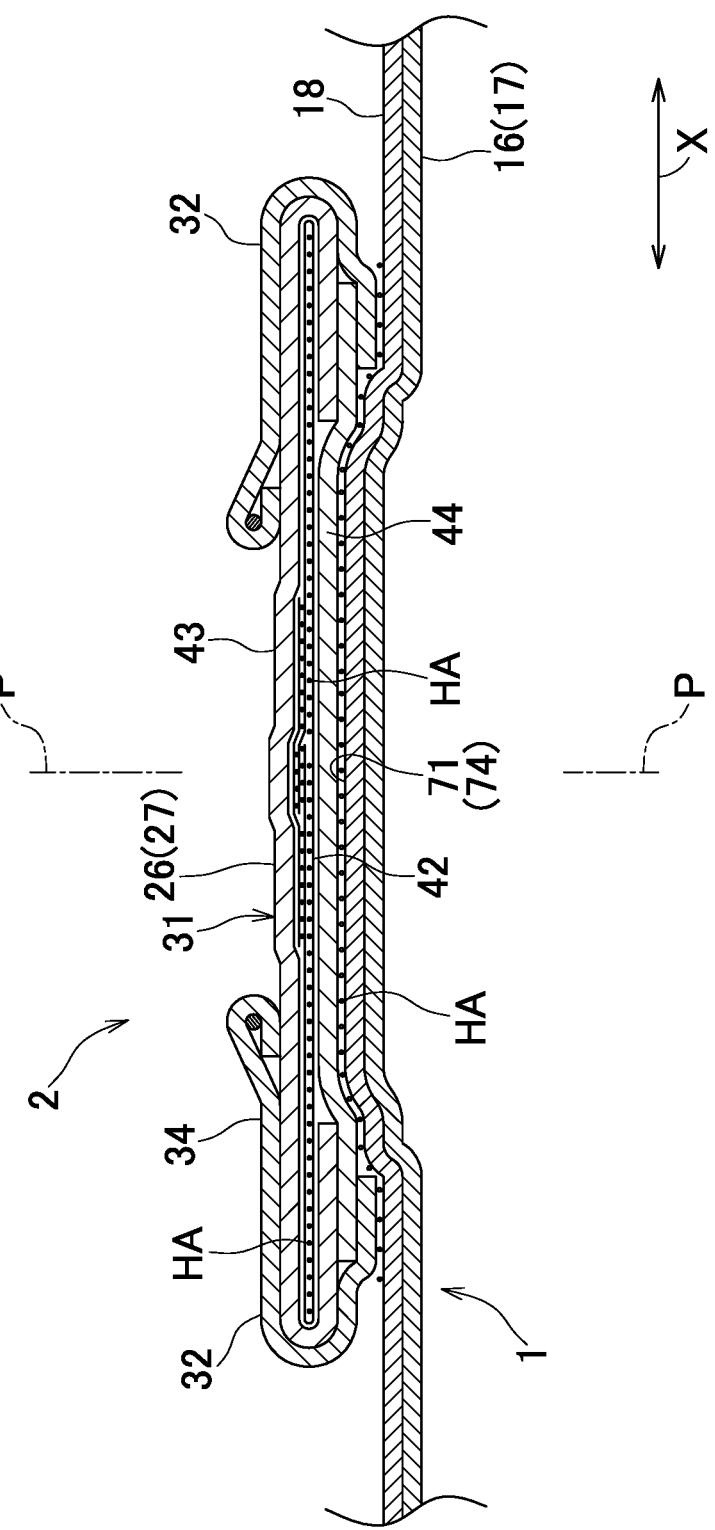
FIG. 7 is a sectional view taken along line S1 or S6 in FIG. 2.

FIGS. 4, 5, 6 and 7 are sectional views in the lateral direction X of the lower torso cover 1 and the absorbent chassis 2 illustrated in FIG. 2 wherein FIG. 4 is a sectional view taken along line S4 indicated in FIG. 2 (the line S4 coincides with the center line Q in FIG. 2), FIG. 5 is a sectional view taken along line S3 or S5, FIG. 6 is a sectional view taken along line S2 and FIG. 7 is a sectional view taken along line S1 or S6.

Referring to FIG. 4, the absorbent structure 31 in the absorbent chassis 2 includes an absorbent body 40 formed of a core 41 prepared in the form of an aggregation of liquid-absorbent materials at least containing wood fluff pulp and polymer particles and a liquid-permeable cover sheet 42 covering the core 41, a liquid-permeable bodyside liner 43 covering the top surface of the core 41 by the cover sheet 42 and a liquid-impermeable backsheet 44 covering the bottom surface of the core by the cover sheet 42. An bottom surface 41b of the core 41 facing the central exterior sheet 18 defining the top surface 41a of the lower torso cover 1 is entirely coated with, for example, hot-melt adhesive HA with which the core 41 is fixed to the cover sheet 42. An top surface 41a of the core 41 opposite to the bottom surface 41b is also fixed to the cover sheet 42 along the center line P and in limited ranges on both sides of the center line P, more specifically, lateral regions of the core 41 are not fixed to the cover sheet 42. When the core 10 is intended for a mild incontinence and formed of the pulp and the superabsorbent polymer particles, a mass per unit area of the core 41 as a whole is preferably in a range of 300 to 600 g/m2, a mass per unit area of the pulp is preferably in a range of 60 to 40 g/m2 and a mass per unit area of the superabsorbent polymer particles is in a range of 40 to 60 g/m2. As one of particular examples, it is possible to use the core 41 containing the pulp having a mass per unit area of 300 g/m2 and the superabsorbent polymer particles having a mass per unit area of 200 g/m2 homogenously mixed or layered on top of each other. It is also possible to use the core 41 in which the quantity of the superabsorbent polymer particles is inhomogenously distributed in a lateral direction X and in a longitudinal direction Y of the core 41. For example, the superabsorbent polymer particles may be used with a mass per unit area of 250 g/m2 in the central region in the lateral direction X of the core 41 and with a mass per unit area of 45 g/m2 in the both lateral regions. As the superabsorbent polymer particles, those widely used in the relevant technical field, for example, hydrolysate of starch-acrylonitrile copolymers may be used. In addition, for preparation of the core 41 prior to actual use, the liquid-permeable materials may be mixed together with use of air flow and then deposited within desired shaped molds or the deposited mixture may be water-sprinkled and then compressed under pressure.

As the cover sheet 42, for example, tissue paper or liquid-permeable fibrous nonwoven fabrics may be used. The cover sheet 42 is fixed to the bottom surface 41b of the core 41, for example, with hot-melt adhesive HA and portions of the cover sheet 42 extending laterally beyond the side edges of the core 41 are folded onto the bottom surface 41b of the core 41 to cover the top surface 41a so that respective lateral portions 42a, 42b may place on top of each other in an area defined symmetrically about a center line P bisecting the dimension in the lateral direction of the absorbent chassis 2. The respective lateral portions 42a, 42b are joined to each other and also to the core 41, for example, with hot-melt adhesive HA. An area in which the core 41 is fixed to the cover sheet 42 with hot-melt adhesive HA defines the region in which the aggregation of the liquid-absorbent materials is fixed to the cover sheet 42.

In a preferred core 41, the lateral portions 42a, 42b of the cover sheet 42 placing on top of each other are covered with a liquid-permeable auxiliary cover sheet 45 to prevent the liquid-absorbent materials from getting out through unintentional gaps between the lateral portions 42a, 42b. The auxiliary cover sheet 45 is fixed to the cover sheet 42, for example, with hot-melt adhesive HA.

The core 41 and the cover sheet 42 as described above are kept in close contact with each other along both the lateral portions 46 of the core 41 but not joined to each other. The portions of the cover sheet 42 extending in the lateral direction X and overlapping each other on the bottom surface of the core 41 are joined to each other, for example, with hot-melt adhesive HA. Thus the bottom surface 41b of the core 41 is fully fixed to the cover sheet 42 and the top surface 41 is fixed to the cover sheet 42 in the limited area symmetrically defined about the center line P but, in both the lateral portions 46, the top surface 41 is not covered with hot-melt adhesive. With such arrangement, it is unlikely that, on the top surface 41a of the respective lateral portions 46, the body exudates absorption through the cover sheet 42 may be impeded by the presence of hot-melt adhesive and, in addition, it is also unlikely that movements of the wood fluff pulp and/or the superabsorbent polymer particles forming the top surface 41a, for example, movements of the superabsorbent polymer particles caused by swelling thereof may be impeded by the presence of hot-melt adhesive. The absorbent body 40 including the superabsorbent polymer particles which are smoothly movable as they swell without being impeded by any obstacles may assure a high absorption rate and a high absorbed amount per unit time.

The bodyside liner 43 may be formed of nonwoven fabrics of thermoplastic synthetic fibers or porous plastic films. The backsheet 44 is formed of plastic films, more preferably, of breathable/liquid-permeable plastic films. The bodyside liner 43 and the backsheet 44 are joined to each other, for example, with hot-melt adhesive (not shown) in an area of them overlapping each other. The bodyside liner 43 may be joined to the cover sheet 42, for example, with hot-melt adhesive (not shown) distributed in an appropriate pattern such as spiral-, dotted- or stripe-pattern.

In each of the leakage-barrier cuffs 32, the proximal edge portion 33 is joined to the absorbent structure 31, for example, with hot-melt adhesive (not shown). While FIG. 2 illustrates the distal edge portion 34 as it overlaps the bodyside liner 43, FIG. 3 illustrates the distal edge portion 34 as it spaced. away from the bodyside liner 43 in order to specify the distal edge portion 34 more clearly. With the diaper 10 being in the state illustrated in FIG. 1, the distal edge portion 34 stands up on the absorbent structure as indicated by imaginary lines under contraction of the elastic elements 36 in the portions thereof extending between the front end portion 26 and the back end portion 27 of the absorbent structure 31, more specifically the portions indicated by the imaginary lines 36a in FIG. 3. In this way, the distal edge portion 34 functions as the cuff adapted to prevent body exudates from leaking sideways. The absorbent chassis 2 arranged in this manner as illustrated in FIG. 4 is joined to the lower torso cover 1 in the coated region 73 indicated in FIG. 3.

FIG. 5 is a sectional view taken along the line S3 or the line S5 (see FIG. 2) respectively extending in the absorbent structure 31 across the front end portion 26 or the back end portion 27 of the absorbent chassis 2 overlapping the front waist region 3 or the back waist region 4 of the lower torso cover 1, respectively, in the front or back end. adjoining portions 26b, 27b including the core 41 wherein the sectional view taken along the line S3 is generally identical to the sectional view taken along the line S5. Both the line S3 and the line S5 are the lines extending across the non-coated regions 76, 78 in the lower torso cover 1. As will be apparent from comparison of the sectional view in FIG. 5 to the sectional view in FIG. 4, these two sectional views are identical with respect to a dimension in the lateral direction X, i.e., a width of the rectangular absorbent structure but, in FIG. 5, the core 41 extends over the entire width of the absorbent structure 31 and there is no region in which both the lateral portions 46 of the core 41 lie on top of each other. The core 41 in FIG. 5 has a width larger than that in FIG. 4 and, therefore, both the end portions 46 of the core 41 not joined to the cover sheet 42 respectively have dimensions in the lateral direction X larger than dimensions in the lateral direction X of both the end portions 46 in FIG. 4. A state in which the leakage-barrier cuffs 32 are attached to the absorbent structure 31 is identical to that in FIG. 4. The backsheet 31 and the central exterior sheet 18 facing each other are not joined to each other and the front exterior sheet 16 or the back exterior sheet 17 is joined to the outside of the central exterior sheet 18, for example, with hot-melt adhesive (not shown).

FIG. 6 is a sectional view taken along the line S2 (See FIG. 3) extending across the coated regions 72 and the non-coated regions 76 in the lower torso cover 1. The coated regions 72 are provided so that both the laterals of the front end adjoining portion of the front end portion 26 in the absorbent chassis 2 including the core 41 may be partially joined to the lower torso cover 1. Depending on a size of the diaper 10, each of the coated regions preferably has a dimension in the lateral direction X in a range of 5 to 20 mm and a dimension in the longitudinal direction Y in a range of 10 to 30 mm as viewed in FIG. 3 so that at least one of the front waist elastic elements 21 may extend between the coated regions 72, 72. Contraction of this front waist elastic element 21 extending in this manner directly and exclusively acts on both the laterals of the absorbent chassis 2 to get close both the laterals to each other in the lateral direction X, thereby to reduce an apparent width of the absorbent chassis 2 and to gear up deformation of the absorbent chassis 2 in such a manner that the central portion in the lateral direction X of the absorbent chassis 2 may protrude outward.

FIG. 7 is a sectional view of the absorbent chassis 2 taken along line S1 or line S6 extending across the front end portion 26a or the back end portion 27a not including the core 41 defined in the front end portion 26 or the back end portion 27, respectively, of the absorbent chassis 2. In this regard, the cross-section taken along the line S1 and the cross-section taken along the line S6 are generally identical to each other. Referring to FIG. 7, the portions of the cover sheet 42 extending outward in the longitudinal direction Y beyond the core 41 are joined to each other with hot melt adhesive HA. The bodyside liner 43 and the backsheet 44 are joined to the cover sheet 42 overlapping therewith, for example, with hot melt adhesive (not shown). The backsheet 44, the leakage-barrier cuffs 32 and the central exterior sheet 18 are joined to each other with hot melt adhesive HA in the coated region 71 or the coated region 74. The central exterior sheet 18 and the front exterior sheet 16 or the back exterior sheet 17 placing on top of each other are joined to each other, for example, with hot melt adhesive (not shown). The distal edge portions 34 of the respective leakage-barrier cuffs 32 overlap the bodyside liner 43 and are joined to the bodyside liner 43, for example, with hot melt adhesive (not shown).

Figure 8:
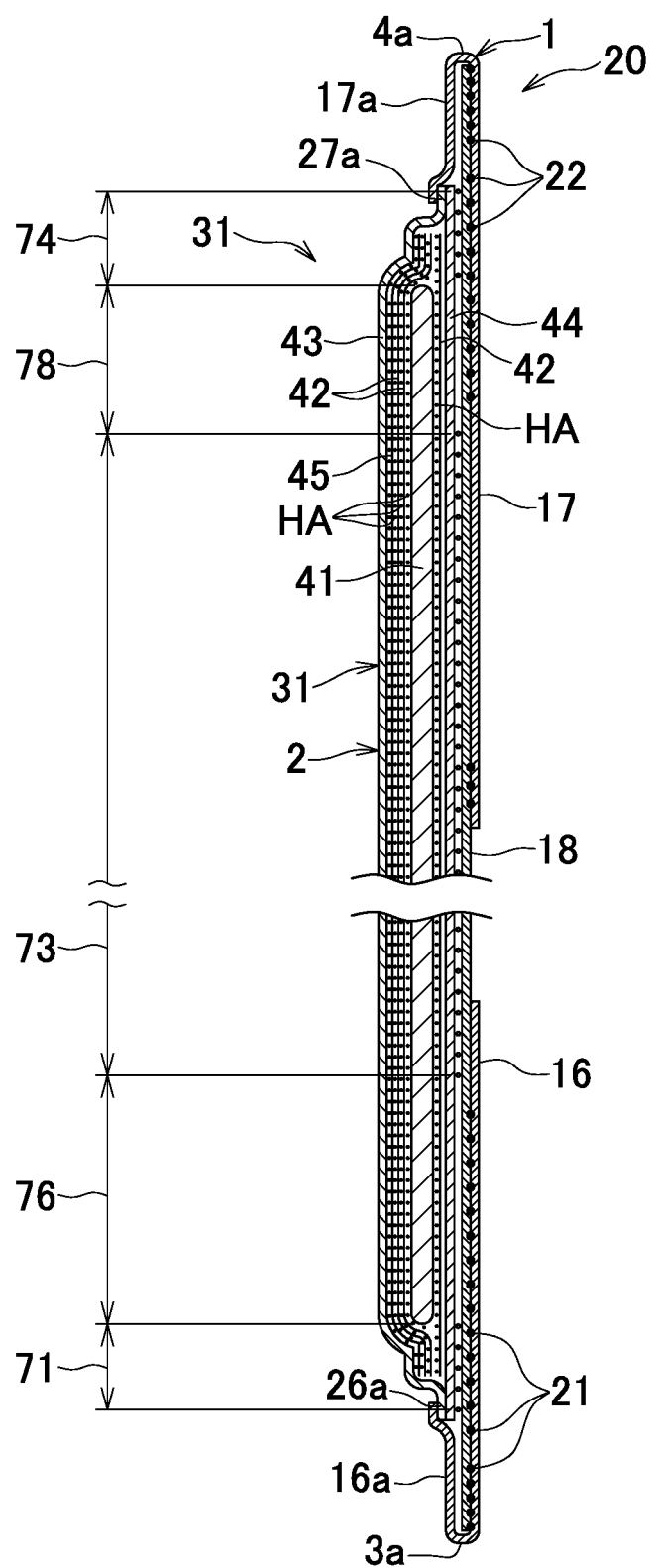
FIG. 8 is a sectional view taken along line S0 in FIG. 2.

FIG. 8 is a sectional view of the absorbent structure 31 taken along line S0 indicated in FIG. 2 wherein the line S0 coincides with the center line P indicated in FIG. 2. In FIG. 8, the coated regions 71, 73, 74 and the non-coated regions 76, 78 observed along the line S0 are indicated. In the absorbent structure 31, the cover sheet 42, the auxiliary cover sheet 45, the bodyside liner 43 and the backsheet 44 extend outward beyond the core 41, overlap with each other and are joined to each other, for example, with hot-melt adhesive HA. Respective portions of the bodyside liner 43 and the backsheet 44 extending outward beyond the core 41 define the front and back end portions 26a, 27a (see FIG. 2) in the front end portion 26 and the back end portion 27 of the absorbent chassis 2. The central exterior sheet 18 and the front exterior sheet 16 joined to each other are joined to the absorbent chassis 2 in the coated region 71 and the central exterior sheet 18 and the back exterior sheet 17 joined to each other are joined to the absorbent chassis 2 in the coated region 74. The portion 16a of the front exterior sheet 16 extending outward beyond the central exterior sheet 18 and the portion 17a of the back exterior sheet 17 extending outward beyond the central exterior sheet 18 are folded back along the respective edges of the central exterior sheet 18 so as to overlap the central exterior sheet 18 and the absorbent chassis 2 and are joined to these central exterior sheet 18 and absorbent chassis 2, for example, with hot melt adhesive (not shown). The front exterior sheet 16 and the back exterior sheet 17 folded back in this manner to form the peripheries 3a, 4a of the waist-opening 12 of the diaper 10 (see FIG. 1). Between the central exterior sheet 18 and the front exterior sheet 16 and between the central exterior sheet 18 and the back exterior sheet 18, the front waist elastic elements 21 and the back waist elastic elements 22 are interposed, respectively. In a preferred embodiment of these front and back waist elastic elements 21, 22, LUCRA™ 4.5 K CIS is used at a stretch ratio in a range of 1.5 to 3. In a further preferred embodiment of the elastic elements 21, 22, the stretch ratio of the elastic elements 21, 22 are arranged so as to be reduced in a step-by-step from the peripheries 3a, 4a toward the crotch region 5. The elastic elements 21, 22 used in such manner, particularly the front waist elastic elements 21 function to facilitate the central portion in the lateral direction X of the absorbent chassis 2 to protrude forward so that the central portion may smoothly receive the male sex organ.

Figure 9:
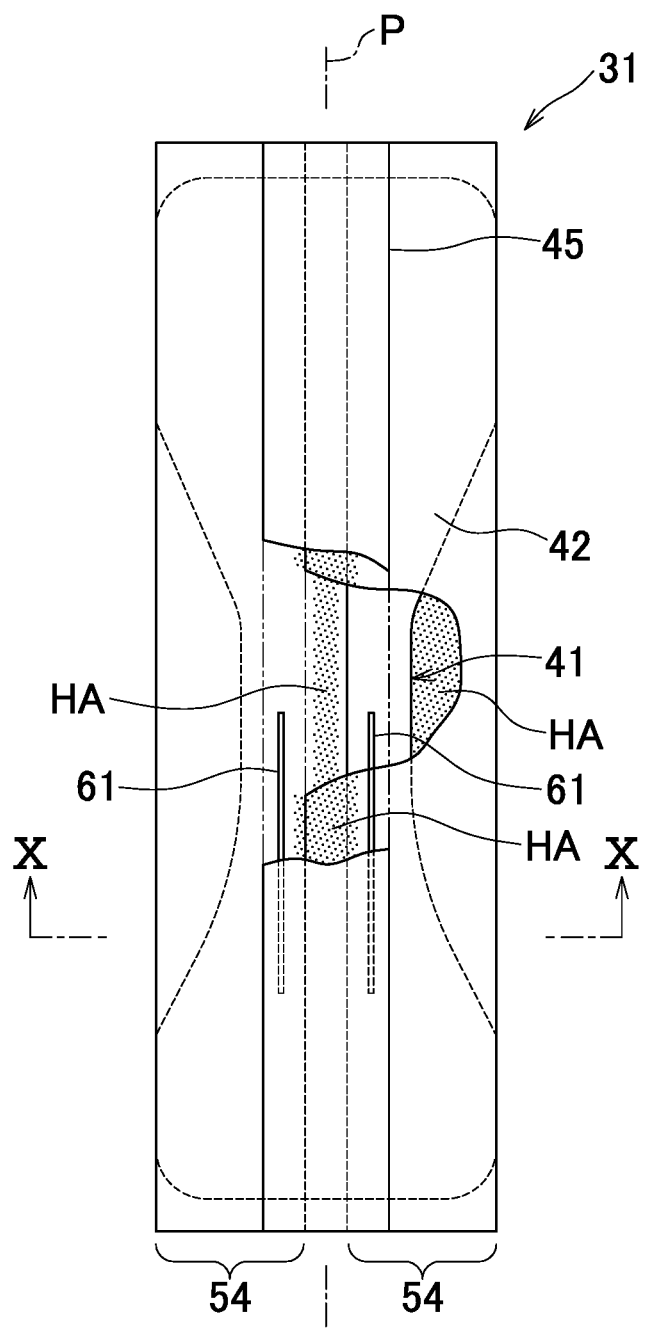
FIG. 9 is a partially cutaway plan view illustrating the absorbent structure according to one embodiment.
Figure 10:
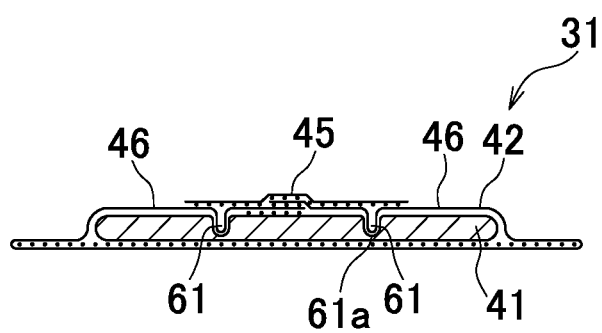
FIG. 10 is a sectional view taken along line X-X in FIG. 9.

FIGS. 9 and 10 are a partially cutaway plan view of the absorbent structure 31 according to one embodiment and a sectional view thereof taken along line X-X in FIG. 8, respectively. In the absorbent structure 31 illustrated therein, the core 41 and the cover sheet 42 are formed with a plurality of compressed grooves 61 which are then covered with the cover sheet 42 to form these compressed grooves 61, the core 41 may be locally compressed together with the cover sheet 42 in the direction from the top surface 41*a* toward the bottom surface 41*b* (see FIG. 4) of the core 41. In bottoms 61*a* of the respective compressed grooves 61, the liquid-absorbing materials such as the superabsorbent polymer particles are also in compressed state and, in other words, a density of the core 41 is higher in the bottoms 61*a* than a density of the core 41 in peripheral regions of the respective compressed grooves 61. The preferred compressed grooves 61 are formed symmetrically about the center line P in the area in which the core 41 and the cover sheet 42 are joined to each other with hot melt adhesive HA. Preferably, the compressed grooves 61 are formed in the crotch region 5 defined between the front waist region 3 and back waist region 4 of the lower torso cover 1. If it is intended to form only one pair of the compressed grooves 61, these compressed grooves will be preferably formed in an anterior portion of the crotch region 5. When the diaper 10 is used as men's diaper, the diaper 10 may be put on the wearer's body so that the wearer's male organ may be set in a space defined between the pair of the compressed grooves 61 formed in the anterior portion of the crotch region 5. In this way, a desired fit of the absorbent chassis 2 to the wearer's body and therefore a good wear comfort of the diaper 10 are ensured. The auxiliary cover sheet 45 in the absorbent structure 31 well functions to prevent occurrence of a trouble such that the absorbent materials such as the wood fluff pulp and the superabsorbent polymer particles may leak out through tears of the cover sheet 42 and get into contact with the wearer's skin.

The disclosure relating to the present invention described hereinabove may be arranged at least as follows.

A disposable pull-on diaper having a lateral direction and a longitudinal direction and including a lower torso cover which assumes a tubular shape in use and defines at least a front waist region, a back waist region among the front waist region, the back waist region and a crotch region, an absorbent chassis which is provided with an absorbent structure and extends between the front waist region and the back waist region and having a front end portion and a back end portion adapted to overlap the front waist region and the back waist region, respectively, a waist opening and a pair of leg-openings, wherein that:

the lower torso cover has an elastic region in which a plurality of elastic elements extend in a lateral direction of the lower torso cover and contractibly secured thereto under tension;

the absorbent chassis includes an absorbent body contained within the absorbent structure, a liquid-permeable bodyside liner and a liquid-impermeable backsheet and includes a cover sheet to cover the absorbent body wherein the cover sheet extends outward in the longitudinal direction beyond the absorbent body;

the front end portion of the absorbent chassis has a front end portion joined to the lower torso cover in the elastic region and a front end adjoining portion not joined to the elastic region and extending adjacent to the front end portion on the side of the crotch region wherein an area extending adjacent to the front end adjoining portion on the side of the crotch region is joined to an inelastic region extending adjacent to the front end adjoining portion on the side of the crotch region and including none of the elastic elements extending in the lateral direction; and the absorbent body extends at least from the crotch region to the front end adjoining portion and the front end portion is defined by the portion of the cover sheet extending outward beyond the absorbent body.

Though not illustrated, it is possible to make the lower torso cover by separately forming a first element corresponding to the front waist region 3, a second element corresponding to the back waist region 4 and a third element corresponding to the crotch region 5 and thereafter joining the third element to the first and second elements.

The disposable pull-on type diaper according to the present invention summarized in the above paragraph may include embodiments at least as described below and these embodiments may be taken in isolation or in combination.

(1) The front end adjoining portion in the front end portion has both laterals opposite to each other in the lateral direction of the lower torso cover and the respective laterals are partially joined to the elastic region.

(2) The front end adjoining portion of the absorbent body is provided with a plurality of compressed grooves arranged at intervals and extending in the longitudinal direction symmetrically a center line bisecting the dimension in a lateral direction orthogonal to the longitudinal direction of the diaper.

(3) The absorbent chassis is provided at both laterals thereof with leakage-barrier cuffs each extending in the longitudinal direction and having a proximal edge portion and a distal edge portion and wherein the distal edge portion is arranged so as to be elastically contractible in the longitudinal direction and one end portion thereof in the longitudinal direction is located at the front end adjoining portion in the front end portion.

(4) The absorbent body is formed of absorbent core and a liquid-permeable cover sheet wrapping the absorbent core and, between each pair of the adjacent compressed grooves as viewed in the lateral direction, the cover sheet overlaps with itself.

(5) Both the lower torso cover and the absorbent chassis include none of elastic elements extending in the lateral direction on the side of the elastic region in the lower torso cover close to the crotch region.

REFERENCE SIGNS LIST

1 lower torso cover
2 absorbent chassis
3 front waist region
4 back waist region
5 crotch region
10 pull-on diaper
12 waist-opening
13 leg-openings
21 elastic elements
22 elastic elements
26 front end portion
26*a* front end edge
26*b* front end adjoining portion
27 back end portion
31 absorbent structure
32 leakage-barrier cuffs
33 proximal edge portions 34 distal edge portions
40 absorbent body
41 core
42 cover sheet
43 bodyside liner
44 backsheet
61 compressed grooves
P center line

The invention claimed is:

1. A disposable pull-on diaper having a lateral direction and a longitudinal direction-comprising:
  a lower torso cover that assumes a tubular shape and defines at least a front waist region and a back waist region among the front waist region, the back waist region and a crotch region;
  an absorbent chassis that comprises absorbent structure, extends between the front waist region and the back waist region, and has a front end portion and a back end portion adapted to overlap the front waist region and the back waist region, respectively;
  a waist opening; and
  a pair of leg-openings, wherein,
  the lower torso cover has an elastic region in which a plurality of elastic elements extend in the lateral direction and contractibly secured thereto under tension,
  the absorbent chassis comprises by an absorbent body included in the absorbent structure, a liquid-permeable bodyside liner and a liquid-impermeable backsheet and includes a cover sheet to wrap the absorbent body wherein the cover sheet extends outward in the longitudinal direction beyond the absorbent body,
  the front end portion of the absorbent chassis has:
    a front end portion joined to the lower torso cover in the elastic region; and
    a front end adjoining portion extending adjacent to the front end portion on the side of the crotch region,
  an area extending adjacent to the front end adjoining portion on the side of the crotch region is joined to an inelastic region extending adjacent to the front end adjoining portion on the side of the crotch region and including none of elastic elements extending in the lateral direction,
  the absorbent body extends at least from the crotch region to the front end adjoining portion and the front end portion is defined by the portion of the cover sheet extending outward beyond the absorbent body,
  the front end adjoining portion in the front end portion has two laterals that overlap with the elastic region and are opposite to each other in the lateral direction and each of the two laterals is partially but not completely joined to the elastic region, and
  an area extending in the lateral direction between the two laterals overlaps with the elastic region and is not joined to the elastic region.

2. The diaper according to claim 1, wherein the front end adjoining portion of the absorbent body is provided with a plurality of compressed grooves arranged at intervals and extending in the longitudinal direction symmetrically a center line bisecting a dimension in the lateral direction.

3. The diaper according to claim 1,
  wherein the absorbent chassis comprises a pair of leakage-barrier cuffs each extending in the longitudinal direction,
  wherein the pair of leakage-barrier cuffs are disposed at both laterals of the absorbent chassis, respectively,
  wherein each of the pair of leakage-barrier cuffs comprises a proximal edge portion and a distal edge portion, and
  wherein the distal edge portion is arranged so as to be elastically contractible in the longitudinal direction and one end portion of the distal edge portion in the longitudinal direction is located at the front end adjoining portion in the front end portion.

4. The diaper according to claim 2, wherein the absorbent body is formed of absorbent core and a liquid-permeable cover sheet wrapping the absorbent core and, between each pair of the adjacent compressed grooves as viewed in the lateral direction, the cover sheet overlaps with itself.

5. The diaper according to claim 1, wherein both the lower torso cover and the absorbent chassis include none of elastic elements extending in the lateral direction on the side of the elastic region in the lower torso cover close to the crotch region.

* * * * *